US006506783B1

(12) United States Patent
Camden

(10) Patent No.: US 6,506,783 B1
(45) Date of Patent: *Jan. 14, 2003

(54) CANCER TREATMENTS AND PHARMACEUTICAL COMPOSITIONS THEREFOR

(75) Inventor: James Berger Camden, West Chester, OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/857,811

(22) Filed: May 16, 1997

(51) Int. Cl.⁷ ............................................ A61K 31/415
(52) U.S. Cl. ...................................... 514/388
(58) Field of Search ......................................... 514/388

(56) References Cited

U.S. PATENT DOCUMENTS

| | | | | |
|---|---|---|---|---|
| 3,010,968 A | 11/1961 | Loux | ...................... | 260/309.2 |
| 3,370,957 A | 2/1968 | Wagner et al. | .............. | 514/388 |
| 3,499,761 A | 3/1970 | Dersch | | |
| 3,541,213 A | 11/1970 | Klopping | .................... | 424/273 |
| 3,669,969 A | 6/1972 | Lunn | ...................... | 260/256.4 |
| 3,738,995 A | 6/1973 | Adams et al. | ........... | 260/309.2 |
| RE28,403 E | 4/1975 | Actor et al. | | |
| 3,881,014 A | 4/1975 | Regel et al. | ................ | 424/273 |
| 3,956,262 A | 5/1976 | Heyes et al. | ................ | 260/140 |
| 4,046,906 A | 9/1977 | Frensch et al. | ............. | 414/273 |
| 4,086,235 A | 4/1978 | Beard | | |
| 4,731,366 A | 3/1988 | Munro et al. | ................ | 514/278 |
| 4,814,329 A | 3/1989 | Harsanyi et al. | ............ | 514/211 |
| 5,098,923 A | 3/1992 | Karjalainen et al. | ........ | 514/396 |
| 5,114,951 A | 5/1992 | King | .......................... | 514/388 |
| 5,149,527 A | 9/1992 | Weisenthal | | |
| 5,284,662 A | 2/1994 | Koparkar et al. | | |
| 5,290,801 A | 3/1994 | Higley et al. | ................ | 514/395 |
| 5,310,748 A | 5/1994 | Wilde et al. | ................. | 514/397 |
| 5,329,012 A | 7/1994 | Anderson | ................. | 548/318.5 |
| 5,364,875 A | 11/1994 | Wilde | .......................... | 514/375 |
| 5,434,163 A | 7/1995 | Edlind et al. | ............... | 514/310 |
| 5,441,742 A | 8/1995 | Autant et al. | | |
| 5,554,373 A | 9/1996 | Seabrook | | |
| 5,629,341 A | 5/1997 | Camden | | |
| 5,656,615 A | 8/1997 | Camden | | |
| 5,665,713 A | 9/1997 | Camden | | |
| 5,665,751 A | 9/1997 | Camden | | |
| 5,767,138 A | 6/1998 | Camden | | |
| 5,770,616 A | 6/1998 | Camden | | |
| 5,840,742 A | 11/1998 | Camden | | |
| 5,854,231 A | 12/1998 | Camden | | |
| 5,872,142 A | 2/1999 | Camden | | |
| 5,880,144 A * | 3/1999 | Camden | ...................... | 514/397 |
| 5,900,429 A * | 5/1999 | Camden | ...................... | 514/395 |
| 5,902,804 A | 5/1999 | Camden | | |
| 5,908,855 A | 6/1999 | Camden | | |
| 5,929,099 A * | 7/1999 | Camden | ...................... | 514/365 |
| 5,932,604 A | 8/1999 | Camden | | |
| 5,932,609 A | 8/1999 | Camden | | |
| 6,025,377 A | 2/2000 | Camden | | |
| 6,077,862 A | 6/2000 | Camden | | |

FOREIGN PATENT DOCUMENTS

| | | | |
|---|---|---|---|
| BE | 667158 | 11/1965 | |
| EP | 617968 | 10/1994 | |
| FR | 2155888 | 5/1973 | |
| GB | 1123317 | 8/1968 | |
| WO | WO/94 04541 | 3/1994 | |
| WO | WO 96/32103 | 10/1996 | |
| WO | WO 96/32104 | 10/1996 | |
| WO | WO 96 32107 | 10/1996 | .................. 31/425 |
| WO | WO 96/32107 | 10/1996 | |
| WO | WO 96/32115 | 10/1996 | |
| WO | WO 96/40119 | 12/1996 | |
| WO | WO 96/40120 | 12/1996 | |
| WO | WO 96/40122 | 12/1996 | |
| WO | WO 97/05872 | 2/1997 | |
| WO | WO 97/05873 | 2/1997 | |
| WO | WO 97/05870 | 4/1997 | |
| WO | WO 98/32440 | 7/1998 | |
| WO | WO 98/51303 | 11/1998 | |
| WO | WO 98/51304 | 11/1998 | |
| WO | WO 99/59585 | 11/1999 | |
| WO | WO 00/21504 | 4/2000 | |
| WO | WO 00/50007 | 8/2001 | |

OTHER PUBLICATIONS

Chemical Abstracts 65:6570h referring to BE patent, date unknown.
Chemical Abstracts 113:112365 (1990) Ghannoum, et al.
Chemical Abstracts 121:175012z, (1994) p 607, Katiyar, et al.
Lapras, M. et al. Bull. Soc. Sci. Vet. et Med. comparee, Lyon, 1975, vol. 77, No. 6, pp. 379–397 (in French)—and English translation thereof.

(List continued on next page.)

Primary Examiner—Jerome D. Goldberg
(74) Attorney, Agent, or Firm—Bart S. Hersko

(57) ABSTRACT

A pharmaceutical composition that inhibits the growth of tumors and cancers in mammals and can be used to treat viral infections that comprises a fungicide is disclosed. The particular fungicide used is a benzimidazole derivative having the formula:

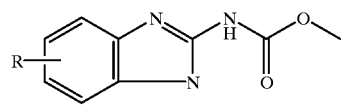

wherein R is selected from the group consisting of H, carboxyl ($-CO_2H$), hydroxyl, amino or esters ($-CO_2R'$) wherein R' is selected from the group consisting of alkoxy, haloalkyl, alkenyl, and cycloalkyl wherein the alkyl groups have from 1–8 carbons or $CH_3CH_2(OCH_2CH_2)_n-$ or $CH_3CH_2CH_2(OCH_2CH_2CH_2)_n-$ or $(CH_3)_2CH-(OCH(CH_3)CH_2)_n-$ wherein n is from 1–3, the pharmaceutically acceptable salts thereof, or mixtures thereof.

12 Claims, No Drawings

OTHER PUBLICATIONS

Teicher, et al., Breast Cancer Research and Treatment, vol. 36, No. 2, pp. 227–236 (1995).

Bissery, et al., Seminars in Oncology: Management of Breast Cancer: A New Therapeutic Approach, vol. 22, No. 6–S13, pp. 3–16, (1995).

Private Communication to Dr. Von Hoff from National Institute of Health, National Cancer Society (1995).

Chemical Abstracts 92:123231 (1979) Menzel et al.

Lacey et al., International Journal for Parasitology, vol. 18 No. 7, pp. 885–936 (1988).

Merck Index, 12$^{th}$ ed., 7943 and 9877, Merck & Co. (NJ 1996).

Chemical Abstracts 102:217569 (1985) Elgebaly et al.

Chemical Abstracts 87:161659 (1997) Lundy et al.

Lacey, et al., Biochemical Pharma., vol. 34, No. 7, pp. 1073–1077 (1985).

Lassnau, et al., Chest, vol. 104, pp. 119–122 (1993).

Carter et al., Chemotherapy of Cancer, 2$^{nd}$ Ed., John Wiley & Sons, NY, NY (1981), pp. 362–365.

Brown et al J. Am. Chem. Soc. 83, pp. 1764–1765 (1961).

Grenda, et al. J. Org. Chem. 30, 259 (1965).

Georgopapadakov, et al. Science, vol. 264, pp. 371–373 (Apr. 15, 1994).

W.T. Thompson, Agricultural Chemicals Book IV, Fungicides, pp. 154, 121, 123.

Carter, W.A. CRC Press, Selective Inhibitors of Viral Functions, pp. 277–346 (1975).

Nene. et al., International Science Publisher, Fungicides in Plant Disease Control, Chapter 9, 1993.

Merck Index, Eighth Edition, 1968, p 1035.

Delatour et al., Therapie, vol. 31, No. 4., pp. 505–515, (1976).

Eigebaly et al., J. Natl. Cacner Inst., vol. 74, No. 4, pp. 811–815 (1985).

DuPont, Material Safety Data Sheet Benlate Fungicide, Sep. 27, 1994.

NASR et al., "Computer Assisted Structure–Anticancer Activity Correlations of Carbamates and Thiocarbamates-"Journal of Pharmaceutical Sciences, pp. 831–836, (1985), American Pharmeutical Association.

SETOI et al., "Preparation of benzamide derivatives having a vasopressin antagonistic activity", Chemical Abstract 129:67773, ( 1998), American Chemical Society.

* cited by examiner

CANCER TREATMENTS AND PHARMACEUTICAL COMPOSITIONS THEREFOR

TECHNICAL FIELD

This invention is a pharmaceutical composition that is effective in the treatment of HIV and other viral infections and inhibits the growth of cancers and tumors in mammals, particularly in human and warm blooded animals. The composition contains a benzimidazole derivative, the pharmaceutically acceptable salts thereof or mixtures thereof with other viral cancer treatments.

BACKGROUND OF THE INVENTION

HIV and other viral infections are one leading cause of death. HIV is a disease in which a virus is replicated in the body which attacks the body's immune system. The HIV virus is not easily destroyed nor is there a good mechanism for keeping the host cells from replicating the virus. Herpes Simplex is another viral infection which is difficult, if not impossible, to cure. A method of treating these diseases and other viral infections in highly desirable. Clearly a material which would target the HIV virus and inhibit viral replication is highly desirable.

Cancers are a leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolics form the bulk of therapies available to oncologists. Ideally cytotoxic agents that have specificity for cancer and tumor cells while not affecting normal cells would be extremely desirable. Unfortunately, none have been found and instead agents which target especially rapidly dividing cells (both tumor and normal) have been used.

Clearly, the development of materials that would target tumor cells due to some unique specificity for them would be a breakthrough. Alternatively, materials that were cytotoxic to tumor cells while exerting mild effects on normal cells would be desirable. Therefore, it is an object of this invention to provide a pharmaceutical composition that is effective in inhibiting the growth of tumors and cancers in mammals with mild or no effects on normal cells.

More specifically, it is an object of this invention to provide an anti-cancer composition comprising a pharmaceutical carrier and a benzimidazole derivative as defined herein along with a method for treating such cancers.

These compositions are also effective against viruses and can be used to treat viral infections. Therefore it is another object of this invention to provide a method of treating viral infections such as HIV, influenza and rhinoviruses.

These and other objects will become evident from the following detailed description of this inventions.

A pharmaceutical composition for treatment of viral infections and cancer in mammals, and in particular, warm blooded animals and humans, comprising a pharmaceutical carrier and an effective amount of compound having the formula.

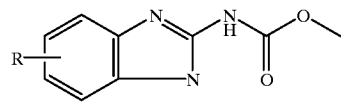

wherein R is selected from the group consisting of H, carboxyl (—$CO_2H$), hydroxyl, amino or esters ($O_2$) wherein R is selected from the group consisting of alkoxy, haloalkyl, alkenyl, and cycloalkyl wherein the alkyl groups have from 1–8 carbons or $CH_3CH_2(OCH_2CH_2)_n$— or $CH_3CH_2CH_2(OCH_2CH_2CH_2)_n$— or $(CH_3)_2CH$— and

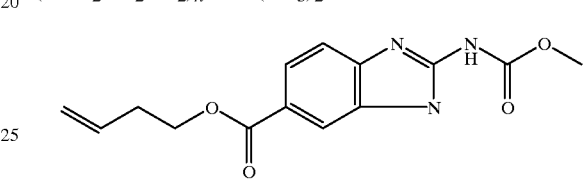

and $(OCH(CH_3)CH_2)_N$—wherein n is from 1–3 or the pharmaceutically acceptable inorganic or organic acid salts thereof, or mixtures thereof. The preferred alkyl groups are straight chain. Preferably the halogen is substituted on the terminal carbon, and the halogen is chlorine. The preferred cycloalkyl groups are those having 3–6 carbon atoms. The cycloalkyl groups also include those which are substituted on an alkyl chain, 2-cyclopropylethyl, cyclopropylmethyl, 2-cyclopropyl propyl or 2-cyclopropylpropyl or cyclohexylmethyl. Preferred compounds are those having the formulas:

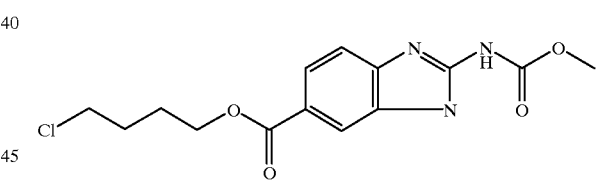

and

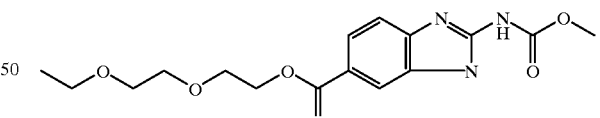

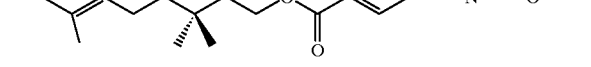

and

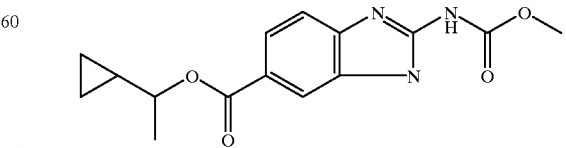

and

-continued

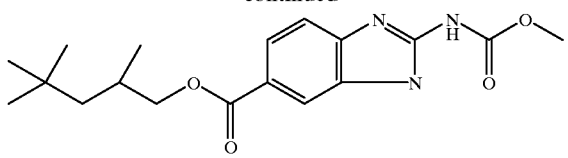

These compositions can be used to inhibit the growth of cancers and other tumors in humans or animals by administration of an effective amount either orally, rectally, topically or parenterally, intravenously or by injection into the tumor.

DETAILED DESCRIPTION OF THE INVENTION

A. DEFINITIONS:

As used herein, the term "comprising" means various components can be conjointly employed in the pharmaceutical composition of this invention. Accordingly, the term "consisting essentially of" and "consisting of" are embodied in the term comprising.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical addition salts"a is salt of the anti-cancer compound with an organic or inorganic acid. These preferred acid addition salts are chlorides, bromides, sulfated, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle for delivering the anti-cancer agent to the animal or human. The carrier may be liquid or solid and is selected with the planned manner of administration in mind.

As used herein, "cancer" refers to all types of cancers or neoplasm or malignant tumors found in mammals, including leukemia.

As used herein, the "anti-cancer compounds" are benzimidazole derivatives, and their salts. The exact benzimidazoles derivatives are described in detail below.

As used herein "chemotherapeutic agents" includes DNA-interactive Agents, Antimetabolites, Tubulin-Interactive Agents, Hormonal agents and others, such as Asparaginase or hydroxyurea.

As used herein, "viruses" includes viruses which cause diseases (viral infection) in man and other warm blooded animals such as HIV virus, herpes, influenza and rhinoviruses.

As used herein "potentiators" are materials such as triprolidine and its cis-isomer and procodazole which are used in combination with the chemotherapeutic agents and benzimidazole derivatives.

As used herein "significantly reduce" means to reduce the mass of the tumor by significant amount. This will usually be to less than 50% of its original mass, and preferably to reduce the mass to non-detectable amounts.

B. THE ANTI-CANCER AND ANTI-VIRAL COMPOUNDS

The anti-cancer and anti-viral compounds are benzimidazole derivatives. These derivatives have the formula:

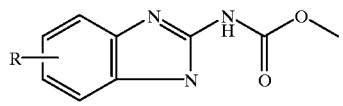

wherein R is selected from the group consisting of H, carboxyl (—CO$_2$H), hydroxyl, amino or esters (—CO$_2$R') wherein R' is selected from the group of alkoxy, haloalkyl, alkenyl, and cycloalkyl wherein the alkyl groups have from 1–8 carbons or CH$_3$CH$_2$(OCH$_2$CH$_2$)$_n$— or CH$_3$CH$_2$CH$_2$(OCH$_2$CH$_2$)$_n$— or (CH$_3$)$_2$CH—(OCH(CH$_3$)CH$_2$)$_n$— wherein n is from 1–3 and the pharmaceutically acceptable organic or inorganic addition salts thereof. The preferred alkyl groups are straight chain. Preferably the halogen is substituted on the terminal carbon, and the halogen is chlorine. The preferred cycloalkyl groups are those having 3–6 carbon atoms. The cycloalkyl groups also include those which are substituted on an alkyl chain, 2-cyclopropylethyl, cyclopropylmethyl, 2-cyclopropyl propyl or 2-cyclopropylpropyl or cyclohexymethyl. Preferred compounds are those having the formulas:

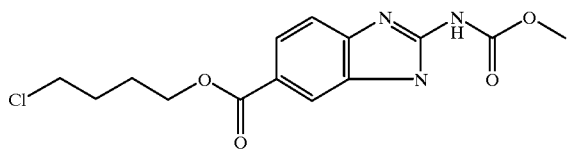

and

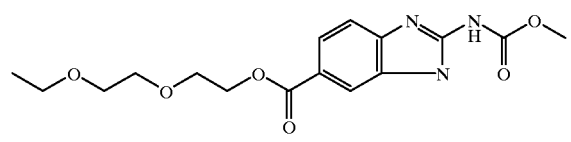

and

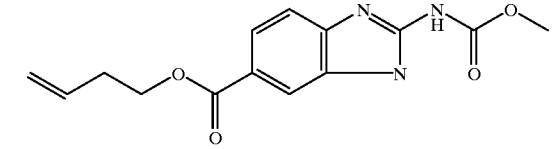

and

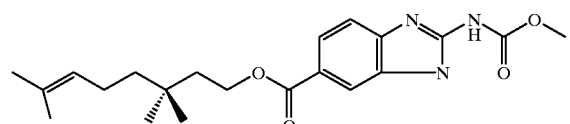

and

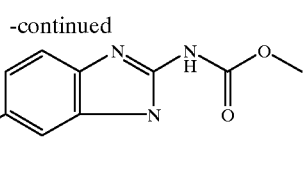

and

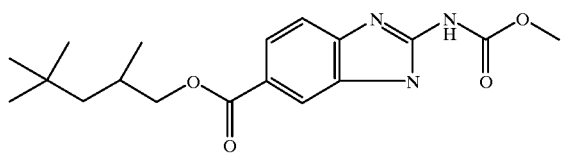

C. HIV DRUGS

HIV is treated with two general classes of drugs, reverse transcriptase inhibitors, and protease inhibitors. AZT is widely used to treat acute HIV. The benzimidazole derivatives and their derivatives can be used in conjunction with AZT for the treatment of acute HIV. They do not interfere with the activity of the AZT.

Other HIV and antiviral agents can be used in conjunction with the therapy provided by this invention. These would include transcriptase inhibitors and protease inhibitors. The drugs can be used concurrently or given in sequence with the benzimidazole derivatives.

D. CHEMOTHERAPEUTIC AGENTS

The benzimidazole derivatives can be administered with chemotherapeutic agents. This can be in sequence, where the chemotherapeutic agent is used to debulk the tumor and then the treatment with the herbicide or fungicide begins, or the two materials can be administered together.

The chemotherapeutic agents are generally grouped as DNA-interactive Agents, Antimetabolites, Tubulin-Interactive Agents, Hormonal agents and others such as Asparaginase or hydroxyurea. Each of the groups or chemotherapeutic agents can be further divided by type of activity or compound. The chemotherapeutic agents used in the sequential method in combination benzimidazole derivatives primarily include members of the DNA-interactive Agents, Antimetabolites, Tubulin-Interactive Agents groups. For a detailed discussion of the chemotherapeutic agents and their method of administration, see Dorr, et al, *Cancer Chemotherapy Handbook,* 2d edition, pages 15–34, Appleton & Lange (Connecticut, 1994) herein incorporated by reference.

In order to reduce the mass of the tumor or stop the growth of the cancer cells, the chemotherapeutic agent must prevent the cells from replicating and also must interfere with the cell's ability to maintain itself. The agents which do this are primarily the DNA-interactive agents such as Cisplatin, and tubulin interactive agents.

DNA-Intreactive Agents include the alklylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as Etoposide and Teniposide; and the DNA minor groove binder Plcamydin.

The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include:

Nitrogen mustards, such as Chlorambucil, Cyclophosphamide, Isofamide, Mechlorethamine, Melphalan, Uracil mustard;

aziridines such as Thiotepa;

methanesulfonate esters such as Busulfan;

nitroso ureas, such as Carmustine, Lomustine, Streptozocin;

platinum complexes, such as Cisplatin, Carboplatin;

bioreductive alkylator, such as Mitomycin, and Procarbazine, Dacarbazine and Altretamine;

DNA strand breaking agents include Bleomycin;

DNA topoisomerase II inhibitors include the following:

Intercalators, such as Amsacrine, Dactinomycin, Daunorubicin, Doxorubicin, Idarubicin, and Mitoxantrone;

nonintercalators, such as Etoposide and Teniposide.

The DNA minor groove binder is Plicamycin,

The antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The antimetabolites useful herein include:

folate antagonists such as Methotrexate and trimetraxate.

pyrimidine antagonists, such as Fluorouracil, Fluorodeoxyuridine, CB3717, Azacytidine, Cytarabine, and Floxuridine purine antagonists include Mercaptopurine, 6-Thioguanine, Fludarabine, Pentostatin;

sugar modified analogs include Cyctrabine, Fludarabine;

ribonucleotide reductase inhibitors include hydroxyurea.

Tubulin Interactive agents act by binding to specific sites on tubulin, a protein that polymerizes to form cellular microtubules. Microtubules are critical cell structure units. When the interactive agents bind on the protein, the cell can not form microtubules Tubulin Interactive agents include Vincristine and Vinblastine, both alkaloids and Paclitaxel.

Adrenal corticosteroids are derived from natural adrenal cortisol or hydrocortisone. They are used because of their anti inflammatory benefits as well as the ability of some to inhibit mitotic divisions and to halt DNA synthesis. These compounds include, Prednisone, Dexamethasone, Methylprednisolone, and Prednisolone.

Hydroxyurea appears to act primarily through inhibition of the enzyme ribonucleotide reductase.

Asparagenase is an enzyme which converts asparagine to nonfunctional aspartic acid and thus blocks protein synthesis in the tumor.

The hormonal agents and leutinizing hormones are not usually used to substantially reduce the tumor mass. However, they can be used in conjunction with chemotherapeutic agents or the benzimidazole derivatives.

Hormonal blocking agents are also useful in the treatment of cancers and tumors. They are used in hormonally susceptible tumors and are usually derived from natural sources. These include:

estrogens, conjugated estrogens and Ethinyl Estradiol and Diethylstilbesterol, Chlorotrianisene and Idenestrol;

progestins such as Hydroxyprogesterone caproate, Medrosyprogesterone, and Megestrol:

androgens such as testosterone, testosterone propionate; fluoxymesterone, methyltesterone;

Leutunizing hormone releasing hormone agents or gonadotropin-releasing hormone antagonists are used primarily the treatment of prostate cancer. These include leuprolide acetate and goserelin acetate. They prevent the biosynthesis of steroids in the tests.

Antihormonal antigens include:

antiestrogenic agents such as Tamosifen, antiandrogen agents such as Flutamide; and antiadrenal agents such as Mitotane and Aminoglutethimide.

E. POTENTIATORS

The "potentiators" can be any material which improves or increases the efficacy of the pharmaceutical composition and/or act on the immune system. One such potentiator is triprolidine and its cis-isomer which are used in combination with the chemotherapeutic agents and the benzimidazole derivatives. Triprolidine is described in U.S. Pat. No. 5,114,951 (1992). Another potentiator is procaodazole, 1H-Benzimidazole-2-propanoic acid;[β-(2-benzimidazole) propionic acid; 2-(2-carboxyethyl) benzimedazole; propazol) Procoadazole is a non-specific active immunoprotective agent against viral and bacterial infections and can be used with the compositions claimed herein.

The potentiators can improve the efficacy of the benzimidazole derivatives and can be used in a safe and effective amount. These combinations can be administered to the patient or animal by oral, rectal or parenteral administration.

Antioxidant vitamins such as ascorbic acid, beta-carotene, vitamin A and vitamin E can be administered with the compositions of this invention.

F. DOSAGE

Any suitable dosage may be given in the method of the invention. The type of compound and the carrier and the amount will vary widely depending on the species of the warm blooded animal or human, body weight, and tumor being treated. Generally a dosage of as little as about 2 milligrams (mg) per kilogram (kg) of body weight and to as much as about 4000 mg per kg of body weight is suitable. Preferably from 15 mg to as much as about 1500 mg/kg of body weight is used. For the chemotherapeutic agents, a lower dosage may be appropriate, i.e., from about 0.01 mg/kg of body weight to about 400 mg/kg body weight, although amounts up to 1500 mg/kg can be used.

Any suitable dosage can be given in the method of the invention for treating HIV. The type of compounds and the carriers and the amount will vary widely depending on the species of the warm blooded animal or human, body weight. The range of the benzimidazoles and their derivatives and the HIV treating agent used will depend on the type of agent. Generally, for the benzimidazoles derivatives and their derivatives a dosage of as little as about 2 milligrams (mg) per kilogram (kg) of body weight to as much as about 4000 mg per kg of body weight is suitable. Higher dosages, up to 6000 mg/kg can also be used. Preferably from 15 mg to as high a level as about 3000 mg/kg of body weight is used for the benzimidazoles derivatives. Generally, the dosage in man is lower than for small warm blooded mammals such as mice. A dosage unit may comprise a single compound or mixtures thereof with other compounds or other cancer inhibiting compounds. For the HIV agents from about 0.01 mg/kg to as much as 1500 mg/kg can be used. Generally, the dosage in man is lower than for small warm blooded mammals such as mice. A dosage unit may comprise a single compound or mixtures thereof with other compounds or other cancer inhibiting compounds. The dosage unit can also comprise diluents, extenders, carriers and the like. The unit may be in solid or gel form such as pills, tablets, capsules and the like or in liquid form suitable for oral, rectal, topical, intravenous injection or parenteral administration or injection into or around the tumor.

G. DOSAGE DELIVERY FORMS

The anti-cancer compounds are typically mixed with a pharmaceutically acceptable carrier. This carrier can be a solid or liquid and the type is generally chosen based on the type of administration being used. The active agent can be coadministered in the form of a tablet or capsule, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from noneffervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297 to Robert, issued Sept. 2, 1975. Techniques and compositions for making dosage forms useful in the present invention are described in the following references: 7 *Modern Pharmaceutics,* Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition (1976).

H. METHOD OF TREATMENT

The method of treatment can be any suitable method which is effective in the treatment of the particular virus, cancer or tumor type that is being treated. Treatment may be oral, rectal, topical, parenteral or intravenous administration or by injection into the tumor and the like. The method of applying or administering an effective amount also varies depending on the tumor or virus being treated. It is believed that parenteral treatment by intravenous, subcutaneous, or intramuscular application of the benzimidazole derivatives formulated with an appropriate carrier. Additional anti-viral materials can be used along with the benzimdazoles derivatives as well as additional cancer inhibiting compound(s) can be combined in the cancer treatments. Diluents can be used to facilitate application or administration is the preferred method of administering the compounds to warm blooded animals.

For the treatment of viral infections, the benzimidazole derivative is administered in doses for 7 to about 21 days or longer if needed to inhibit the growth or to kill the virus. In the case of chronic infections, these agents may need to be given for extended periods of time, up to years.

For the treatment of acute viral infections or HIV, the benzimidazole derivative can be administered after an AZT treatment or in conjunction with other HIV therapies. These drugs can be also administered in a sequential regimen in which the HIV virus is first reduced in the body and then the benzimidazole derivative is administered to keep the virus from continuing to replicate. AZT therapy can be continued during the treatment with the benzimidazole derivatives treatment. If the disease is in the early stages, the benzimidazole derivatives can be administered to keep the virus from replicating or growing and thus slow the progress of the disease.

In cancer treatments, preferably, the benzimidazole derivative is administered first to significantly reduce the size of the cancer or tumor mass. Usually this will take 3 to about 14 days. The reduction in the tumor or level of cancer cells will be to less than 50% of the original level. Radiation therapy may be used in conjunction with benzimidazole derivatives agent treatment.

Once the tumor has been reduced, the benzimidazole derivative is administered. Because of the relative safety of this material, it can be administered for from 14 days to 365 days as needed to maintain its effectiveness in reducing the regrowth of the cancer.

The following examples are illustrative and are not meant to be limiting to the invention.

EXAMPLE 1

Each of the following compounds was used for solubility, growth inhibition in a MTT assay against B16 Murine Melanoma and HT29, reported as IC50($\mu$M), tubulin polymerization inhibition and indirect binding with calf thymus DNA using a Methyl Green displacement. The following results were achieved.

Compound Tested:

| Estimated logP solubility | 1.46 ± 0.60 | |
|---|---|---|
| Growth Inhibitory Activity (MTT Assay) | Cell Line | IC$_{50}$ ($\mu$M) |
| | B16 (Murine Melanoma) | 4.925 |
| | HT29 (Human Colon Carcinoma) | 3.297 |

Compound tested:

| Estimated logP solubility | 1.99 ± 0.89 | |
|---|---|---|
| Growth Inhibitory Activity (MTT Assay) | Cell Line | IC$_{50}$ ($\mu$M) |
| | B16 (Murine Melanoma) | 0.0844 |
| | HT29 (Human Colon Carcinoma) | 0.266 |

Compound tested:

| Estimated logP solubility | 2.93 ± 0.86 | |
|---|---|---|
| Growth Inhibitory Activity (MTT Assay) | Cell Line | IC$_{50}$ ($\mu$M) |
| | B16 (Murine Melanoma) | 0.112 |
| | HT29 (Human Colon Carcinoma) | 0.102 |

Compound tested:

| Estimated logP solubility | 2.72 ± 0.86 | |
|---|---|---|
| Growth Inhibitory Activity (MTT Assay) | Cell Line | IC$_{50}$ ($\mu$M) |
| | B16 (Murine Melanoma) | 0.0440 |
| | HT29 (Human Colon Carcinoma) | 0.00786 |

Compound tested:

| Estimated logP solubility | 5.54 ± 0.87 | |
|---|---|---|
| Growth Inhibitory Activity (MTT Assay) | Cell Line | IC$_{50}$ ($\mu$M) |
| | B16 (Murine Melanoma) | 0.0769 |

Compound Tested:

| Estimated logP solubility | 4.61 ± 0.86 | |
|---|---|---|
| Growth Inhibitory Activity (MTT Assay) | Cell Line | IC$_{50}$ ($\mu$M) |
| | B16 (Murine Melanoma) | 0.0046 |

Compound Tested:

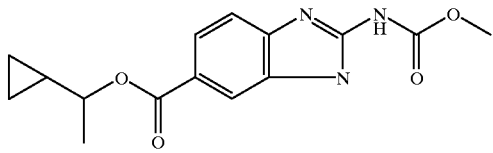

| Estimated logP solubility | 2.69 ± 0.85 | |
|---|---|---|
| Growth Inhibitory Activity (MTT Assay) | Cell Line | IC$_{50}$ ($\mu$M) |
| | B16 (Murine Melanoma) | 0.0621 |

Compound Tested:
What is claimed:

1. A pharmaceutical composition comprising a safe and effective amount of a benzimidazole derivative having the formula:

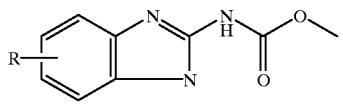

wherein R is —CO$_2$R' and wherein R$_2$' is selected from the group consisting of haloalkyl wherein the alkyl group is selected from C$_{1-8}$alkyl, CH$_3$CH$_2$(OCH$_2$CH$_2$)$_n$—, CH$_3$CH$_2$CH$_2$(OCH$_2$CH$_2$CH$_2$)$_n$—, and (CH$_3$)$_2$CH-(OCH(CH$_3$)CH$_2$)$_n$— wherein n is from 1–3;
a pharmaceutically acceptable organic or inorganic salt thereof; or mixtures thereof.

2. A pharmaceutical composition according to claim 1 comprising a pharmaceutically acceptable carrier and a safe and effective amount of a benzimidazole derivative.

3. A pharmaceutical composition according to claim 1 wherein said pharmaceutically acceptable salt is selected from the group consisting of chlorides, bromides, sulfates, nitrates, phosphates, sulfonates, formates, tartrates, maleates, malates, citrates, benzoates, salicylates, ascorbates and mixtures thereof.

4. A method for treating cancer or a tumor susceptible to treatment comprising administering to a mammal in need thereof a safe and effective amount of a benzimidazole derivative having the formula:

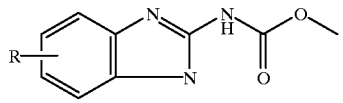

wherein
R is selected from the group consisting of hydroxyl, amino and —CO$_2$R'
wherein R' is selected from the group consisting of haloalkyl wherein the alkyl group is C$_{1-8}$alkyl, CH$_3$CH$_2$(OCH$_2$CH$_2$)$_n$—, CH$_3$CH$_2$CH$_2$(OCH$_2$CH$_2$CH$_2$)$_n$—, and (CH$_3$)$_2$CH—(OCH(CH$_3$)CH$_2$)$_n$—wherein n is from 1–3; or
a pharmaceutically acceptable organic or inorganic salts thereof, or mixtures thereof.

5. A method according to claim 4 comprising a safe and effective amount of pharmaceutically acceptable carrier and a safe and effective amount of a benzimidazole derivative.

6. A method according to claim 4 wherein R is —CO$_2$R' and wherein R' is CH$_3$CH$_2$(OCH$_2$CH$_2$)$_n$— or CH$_3$CH$_2$CH$_2$(OCH$_2$CH$_2$CH$_2$)$_n$— or (CH$_3$)$_2$CH—(OCH(CH$_3$)CH$_2$)$_n$— wherein n is from 1–3.

7. A method according to claim 4 wherein said benzimidazole derivative has the formula:

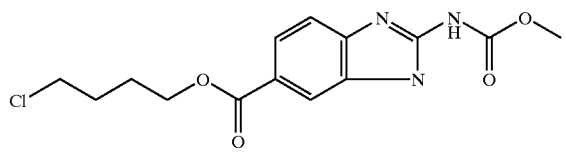

8. A pharmaceutical composition for treating cancer susceptible to treatment comprising a safe and effective amount of a pharmaceutically acceptable carrier and a safe and effective amount of a benzimidazole derivative selected from the group consisting of benzimidazole derivatives having the formula:

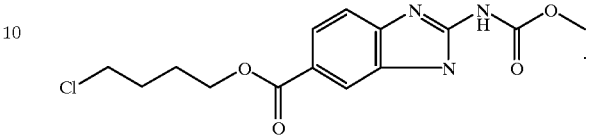

and

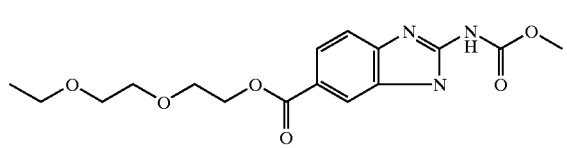

and pharmaceutically acceptable organic or inorganic salts thereof, and mixtures thereof.

9. A pharmaceutical composition according to claim 8 wherein said benzimidazole derivative has the formula:

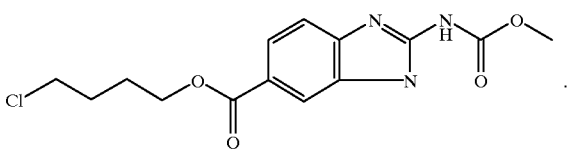

10. A pharmaceutical composition according to claim 8 wherein said benzimidazole derivative is

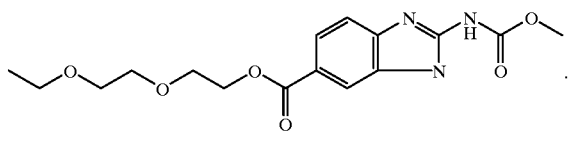

11. A method for treating cancer susceptible to treatment comprising administering to a patient in need thereof a benzimidazole derivative selected from the group consisting of benzimidazole derivatives having the formula:

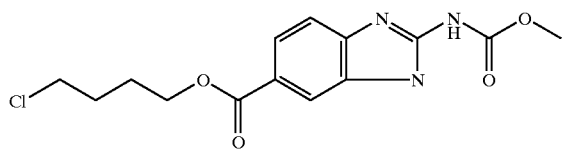

and

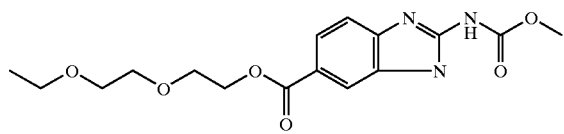

and pharmaceutically acceptable organic or inorganic salts thereof, and mixtures thereof.

12. A method for treating colon cancer comprising administering to a patient in need thereof a safe and effective amount of a benzimidazole derivative having the formula:

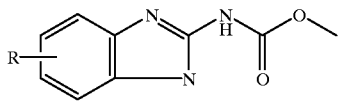

wherein
R is selected from the group consisting of hydroxyl, amino and —CO$_2$R' wherein
R' is haloalkyl wherein the alkyl group of the haloalkyl has from 1–8 carbons, or
CH$_3$CH$_2$(OCH$_2$CH$_2$)$_n$—, or
CH$_3$CH$_2$CH$_2$(OCH$_2$CH$_2$CH$_2$)$_n$—, or
(CH$_3$)$_2$CH—(OCH(CH$_3$)CH$_2$)$_n$— wherein n is from 1–3,
or the pharmaceutically acceptable organic or inorganic salts thereof, or mixtures thereof.

* * * * *

UNITED STATES PATENT AND TRADEMARK OFFICE
CERTIFICATE OF CORRECTION

PATENT NO. : 6,506,783 B1
DATED : January 14, 2003
INVENTOR(S) : James Berger Camden It is certified that error appears in the above-identified patent and that said Letters Patent is hereby corrected as shown below:

Column 11,
Line 17, insert -- is -- immediately after "claimed.";
Line 27, delete the subscript "2" from "$R_2$";
Line 63, delete "salts" and insert therefor, -- salt --;
Line 65, delete entire text of Claim 5, and insert therefor, -- 5. A method according to Claim 4 wherein R is -$CO_2$R' and wherein R' is selected from the group consisting of haloalkyl, $CH_3CH_2(OCH_2CH_2)_n$—, $CH_3CH_2CH_2(OCH_2CH_2CH_2)_n$—, and $(CH_3)_2CH-(OCH(CH_3)CH_2)_n$— wherein n is from 1-3. --

Column 12,
Line 6, delete "4" and insert therefor, -- 11 --.

Signed and Sealed this

Twelfth Day of August, 2003

JAMES E. ROGAN
*Director of the United States Patent and Trademark Office*